United States Patent [19]

Yoshino et al.

[11] Patent Number: 4,727,168

[45] Date of Patent: Feb. 23, 1988

[54] ADHESION PROMOTOR

[75] Inventors: Masachika Yoshino; Hiroshi Inomata; Masayuki Ikeno, all of Gunma, Japan

[73] Assignee: Shin-Etsu Chemical Co., Ltd., Tokyo, Japan

[21] Appl. No.: 774,802

[22] Filed: Sep. 11, 1985

[30] Foreign Application Priority Data

Sep. 14, 1984 [JP] Japan ................. 59-193678

[51] Int. Cl.$^4$ .................. C07F 7/08; C07F 7/10; C07F 7/07
[52] U.S. Cl. .................... 556/408; 556/423; 556/413
[58] Field of Search ............ 556/408, 413, 423

[56] References Cited

U.S. PATENT DOCUMENTS 2,946,701  7/1960  Plueddemann ............. 556/423 X
3,259,518  7/1966  Sterman et al. ........... 556/413 X
3,299,166  1/1967  Emblem et al. ........... 556/413 X
3,448,137  6/1969  Niederprum et al. ....... 556/408

FOREIGN PATENT DOCUMENTS 1143748  3/1985  U.S.S.R. ............... 556/408

Primary Examiner—Paul F. Shaver

Attorney, Agent, or Firm—Jules E. Goldberg

[57] ABSTRACT

The invention provides an efficient method for improving the adhesive bonding strength of various types of rubbery sealant compositions, e.g. room temperature curable silicone rubber composition, to the substrate surface on which it has been cured. The method comprises coating the substrate surface with or admixing the sealant composition before application to the substrate surface with an adhesion promotor which is a reaction product of a reaction mixture comprising:

(a) 1 mole of an organic amine compound having at least one active hydrogen atom in a molecule or an aminoalkyl alkoxysilane compound;
(b) from 0.5 to 4 moles of an organic compound having at least one epoxy group in a molecule or an epoxyalkyl alkoxysilane; and
(c) from 0.5 to 12 moles of an alkoxysilane represented by the general formula $R^1{}_a Si(OR^2)_{4-a}$, in which $R^1$ is a hydrogen atom or a monovalent hydrocarbon group having 1 to 4 carbon atoms, $R^2$ is a monovalent hydrocarbon group having 1 to 4 carbon atoms or an alkoxy-substituted alkyl group and a is a number of zero, 1, 2 or 3, or a partial hydrolysis product thereof, at least one of the components (a) and (b) being an aminoalkyl alkoxysilane or an epoxyalkyl alkoxysilane, respectively.

1 Claim, No Drawings

ADHESION PROMOTOR

BACKGROUND OF THE INVENTION

The present invention relates to an adhesion promotor or, more particularly, to an adhesion promotor having an activity to improve the adhesive bonding of various types of sealants, liquid silicone rubbers and the like to the substrate surface, of which the stability during storage is greatly improved.

As is well known, various types of polymeric sealants are widely used for the purpose of adhesive bonding of electric and electronic parts, sealing or caulking of interstices in building construction works and the like including polyurethane-based and silicone-based ones. A problem in the use of these polymeric sealants is the relatively low adhesive bonding strength thereof to the surface of a substrate made of a metal or plastic resin so that it is a conventional practice that the substrate surface to be adhesively bonded with a sealant is treated in advance with an adhesion promotor or a so-called primer or the sealant is admixed with a small amount of such an adhesion promotor before use.

Several types of adhesion promotors are known in the prior art of which a reaction product of an aminosilane and an epoxysilane is effective according to the disclosure in Japanese Patent Publications Nos. 52-8854 and 55-41702 although an adhesion promotor of this type is defective due to the low stability thereof during storage after preparation to cause eventual gelation or loss of the adhesion-promoting activity within only a few days even at room temperature. The reason for the low stability is presumably the substitution reaction of the alcoholic hydroxy groups produced by the reaction between the amino groups and the epoxy groups for the alkoxy groups of the alkoxysilane as an ingredient of the silicone-based sealant composition to form an inactive cyclic structure or to increase the molecular weight of the silicone component. No effective means, however, has been proposed to solve this problem.

SUMMARY OF THE INVENTION

An object of the present invention is therefore to provide a novel and improved adhesion promotor effective for silicone-based and other types of sealants and free from the above described disadvantage and problem of the conventional adhesion promotors in respect of the stability against degradation during storage.

Thus, the adhesion promotor of the invention is a reaction product of a reaction mixture comprising:

(a) 1 mole of an amine compound having at least one active hydrogen atom in a molecule or an aminoalkyl alkoxysilane compound;

(b) from 0.5 to 4 moles of an organic compound having at least one epoxy group in a molecule or an epoxyalkyl alkoxysilane; and (c) from 0.5 to 12 moles of an alkoxysilane represented by the general formula $R^1_a Si(OR^2)_{4-a}$, in which $R^1$ is a hydrogen atom or a monovalent hydrocarbon group having 1 to 4 carbon atoms, $R^2$ is a monovalent hydrocarbon group or an alkoxy-substituted alkyl group having 1 to 4 carbon atoms and $a$ is a number of zero, 1, 2 or 3, or a partial hydrolysis product thereof, at least one of the components (a) and (b) being an aminoalkyl alkoxysilane or an epoxyalkyl alkoxysilane, respectively.

DETAILED DESCRIPTION OF THE PREFERRED EMBODIMENTS

As is understood from the above given summarizing description, the adhesion promotor of the invention is a reaction product of a reaction mixture comprising the components (a), (b) and (c) in specific proportions discovered as a result of the extensive investigations undertaken by the inventors to establish a means for the stabilization of an adhesion promotor which is of the type of the reaction product between an aminosilane and an epoxysilane. The investigations have led to a discovery that the addition of the alkoxysilane compound as the above given component (c) to the reaction mixture has an effect to block the alcoholic hydroxy groups formed by the reaction between the amino groups and the epoxy groups to leave no free hydroxy groups so that the resultant reaction product can be imparted with greatly improved stability during storage followed by further investigations to complete the present invention.

The component (a) in the reaction mixture for the inventive adhesion promotor is an amine compound having at least one active hydrogen atom in a molecule which may be an aminoalkyl alkoxysilane. Exemplary of the amine compound are organic amine compounds such as ethylamine, diethylamine, propylamine, dipropylamine, allylamine, diallylamine, butylamine, dibutylamine, octylamine, ethylenediamine, hexamethylene diamine, triethylene tetramine, phenylene diamine and the like and aminoalkyl alkoxysilanes represented by the general formula $Z-NH-R^3-SiR^4_m X_{3-m}$, in which $R^3$ is a divalent hydrocarbon group, $R^4$ is a hydrogen atom or a substituted or unsubstituted monovalent hydrocarbon group, $X$ is a hydroxy group or a hydrolyzable group, $Z$ is a hydrogen atom or a group expressed by the formula $-R^3-NH_2$, $R^3$ being as defined above, and $m$ is a number of zero, 1 or 2, such as the compounds expressed by the following structural formulas denoting a methyl, ethyl, phenyl and vinyl groups with the symbols of Me, Et, Ph and Vi, respectively:

(EtO)$_3$Si—(CH$_2$)$_3$—NH$_2$; (EtO)$_2$MeSi—(CH$_2$)$_3$—NH$_2$; (MeO)$_3$Si—(CH$_2$)$_3$—NH$_2$; (EtO)$_3$Si—(CH$_2$)$_3$—NH—(CH$_2$)$_2$—NH$_2$; (MeO)$_3$Si—(CH$_2$)$_3$—NH—(CH$_2$)$_2$—NH$_2$; (MeO)$_2$MeSi—(CH$_2$)$_3$—NH—(CH$_2$)$_3$—NH$_2$; (MeOCH$_2$CH$_2$O)$_3$Si—(CH$_2$)$_3$—NH$_2$;(MeO)$_3$Si—(CH$_2$)$_3$—O—CH$_2$—CHMe—CH$_2$NH$_2$; (EtO)$_3$Si—CH$_2$—CHMe—CH$_2$NH$_2$; (MeO)$_3$Si—CH=CH—CMe$_2$—O—(CH$_2$)$_3$—NH$_2$; (MeO)$_3$Si—(CH$_2$)$_3$—NH—(CH$_2$)$_2$—NH—Et; (MeO)$_3$Si—CH=CH—CMe$_2$—O—(CH$_2$)$_3$—NH—(CH$_2$)$_3$—NH$_2$; (MeO)$_3$Si—(CH$_2$)$_3$—NH—Ph; (MeO)$_3$Si—(CH$_2$)$_3$—NH—(CH$_2$)$_2$—NH—CH$_2$Vi; and (MeO)$_3$Si—(CH$_2$)$_3$—NH—CH$_2$Vi.

In the next place, the component (b) to be reacted with the above described amine compound in the reaction mixture is a compound having at least one epoxy group in a molecule, which may be an epoxyalkyl alkoxysilane compound. Exemplary of the epoxy compound are organic epoxy compounds such as ethylene oxide, propylene oxide, cyclohexene oxide, 4-vinylcyclohexene epoxide, glycidyl ether or ester compounds represented by the general formula

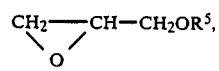

in which $R^5$ is a monovalent hydrocarbon group or an acyl group of the formula —CO—$R^6$, $R^6$ being a monovalent hydrocarbon group, including methyl glycidyl ether, allyl glycidyl ether, butyl glycidyl ether, phenyl glycidyl ether, octyl glycidyl ether, glycidyl methacrylate and the like, and epoxy-containing alkoxysilane compounds represented by the general formula Q—$R^7$—Si$R^8{}_n$(O$R^9$)$_{3-n}$, in which Q is a glycidyloxy group or an epoxycyclohexyl group, $R^7$ is a divalent hydrocarbon group having 1 to 4 carbon atoms, $R^8$ and $R^9$ are each a monovalent hydrocarbon group having 1 to 4 carbon atoms and n is a number of zero, 1, 2 or 3, such as the compounds expressed by the following structural formulas denoting an epoxy group and 3,4-epoxycyclohexyl group with the symbols of Ep and Ec, respectively:

(MeO)$_3$Si—(CH$_2$)$_3$—O—CH$_2$—Ep; (EtO)$_3$Si—(CH$_2$)$_3$—O—CH$_2$—Ep; (MeO)$_2$MeSi—(CH$_2$)$_3$—O—CH$_2$—Ep; (MeO)$_3$Si—CH$_2$CH$_2$—Ec; (MeO)$_3$Si—CH$_2$CH$_2$—Ec; (EtO)$_3$Si—CH$_2$CH$_2$—Ec; Me$_3$Si—(CH$_2$)$_3$—O—CH$_2$—Ep; Me$_3$Si—CH$_2$—Ep; Me$_3$Si—Ep; Me$_3$Si—O—SIMe$_2$CH$_2$—Ep; and

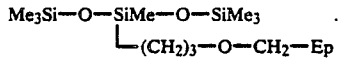

The component (c) to be combined with the above described components (a) and (b) in the reaction mixture to form the inventive adhesion promotor is an alkoxysilane compound represented by the general formula $R^1{}_a$Si(O$R^2$)$_{4-a}$, in which $R^1$ is a hydrogen atom or a monovalent hydrocarbon group having 1 to 4 carbon atoms including alkyl groups such as methyl, ethyl, propyl and butyl groups and alkenyl groups such as vinyl and allyl groups as well as those substituted groups obtained by the replacement of a part or all of the hydrogen atoms in the above named hydrocarbon groups with substituents such as halogen atoms and cyano groups, $R^2$ is a monovalent hydrocarbon group having 1 to 4 carbon atoms exemplified by the same groups as $R^1$ above or an alkoxy-substituted alkyl group and a is zero, 1, 2 or 3. Several of the examples of the alkoxysilane compound suitable as the component (c) include tetramethoxy silane, orthoethyl silicate, tetrapropyl silicate, tetra (2-methoxyethoxy) silane, methyl polysilicate, ethyl polysilicate, trimethoxy silane, methyl diethoxy silane, methyl trimethoxy silane, vinyl trimethoxy silane and the like.

The adhesion promotor of the present invention can be obtained by uniformly blending the above described components (a), (b) and (c) in specified proportions to give a reaction mixture and then heating the mixture under a substantially anhydrous condition to effect the reaction of the components together. As to the blending proportions of the components, the amounts of the components (b) and (c) should be in the ranges of from 0.5 to 4.0 moles and from 0.5 to 12 moles, respectively, per mole of the component (a). When the amount of the component (b) is outside the above mentioned range, no firm adhesive bonding can be obtained by using the resultant reaction product as an adhesion promotor. When the amount of the component (c) is smaller than the above mentioned range, on the other hand, the blocking effect of the free hydroxy groups formed by the addition reaction between the amine compound and the epoxy compound may be incomplete to cause eventual gelation of the reaction product while, when the amount of the component (c) is too large, the addition reaction between the amine compound and the epoxy compound may be disturbed. The reaction is usually complete by heating the reaction mixture for several hours at a temperature in the range from 50° to 180° C. or, preferably, from 90° to 150° C. It is essential that at least one of the components (a) and (b) is an aminoalkyl alkoxysilane or an epoxyalkyl alkoxysilane, respectively, because no sufficient improvement can be obtained in the adhesive bonding when both of the components (a) and (b) are non-silane organic compounds. It is usual that the reaction mixture contains an excessive amount of the alkoxysilane compound as the component (c) so that the reaction product accordingly contains a considerable amount of unreacted alkoxysilane compound which may be removed by distillation under normal pressure or reduced pressure.

The reaction product obtained in the above described manner exhibits excellent adhesion promoting acitvity and, in comparison with similar products in the prior art, is very stable with absolutely no changes in the performance even after storage for 1 month at 40° C. so that the storability thereof would be very long at room temperature to exhibit full activity of adhesion promotion.

In the following, the present invention is described in more detail by way of examples including the description of the preparation of the inventive adhesion promotors and the tests of the adhesion promoting activity thereof. In the following description, the values of the viscosity are all the values obtained by the measurements at 25° C.

PREPARATION 1

Into a flask of 300 ml capacity equipped with a condenser, thermometer and stirrer were introduced 94.5 g (0.4 mole) of 3-glycidyloxypropyl trimethoxysilane and 38.8 g (0.4 mole) of diallylamine and the mixture was heated to a temperature of 90° to 100° C. and agitated at this temperature for 1 hour to effect the reaction between the reactants followed by cooling to room temperature and then dropwise addition of 48.8 g (0.4 mole) of trimethoxysilane so that an exothermic reaction took place with evolution of hydrogen gas.

The thus obtained reaction mixture was subjected to distillation under reduced pressure to give 57.1 g of a fraction boiling at 145° to 150° C. under a pressure of 1 mmHg. This product, referred to as Product I hereinbelow, was identified by the infrared absorption spectrophotometric analysis, NMR spectrometric analysis and mass spectrometric analysis to be a compound expressed, denoting a methyl and a vinyl group with Me and Vi, respectively, by the structural formula

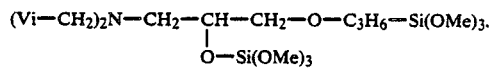

The above mentioned yield was 32% of the theoretical value. This Product I was stable in storage showing no changes after 1 month at 25° C.

PREPARATION 2

Into the same flask as used in Preparation 1 were introduced 94.5 g (0.4 mole) of 3-glycidyloxypropyl trimethoxysilane, 38.8 g (0.4 mole) of diallylamine and 121.7 g (0.8 mole) of tetramethoxysilane and the mixture was heated at 90° to 100° C. under agitation for 2 hours.

Distillation of the reaction mixture under reduced pressure gave 73.1 g of a fraction boiling at 145° to 150° C. under a pressure of 1 mmHg. This product could be identified to be the same compound as the Product I. The above mentioned yield was 41% of the theoretical value.

PREPARATION 3

Into the same flask as used in Preparation 1 were introduced 68.4 g (0.6 mole) of allyl glycidyl ether, 66.5 g (0.3 mole) of 3-aminopropyl triethoxysilane and 136.9 g (0.9 mole) of tetramethoxysilane and the mixture was heated at 90° to 110° C. under agitation for 2 hours to effect the reaction of the reactants. The reaction mixture after completion of the reaction was subjected to distillation under reduced pressure to give 61.0 g of a fraction boiling in the range from 185° to 185° C. under a pressure of 1 mmHg, which is referred to as the Product II hereinbelow. This Product II was identified by the infrared absorption spectrophotometric analysis, NMR spectrometric analysis and mass spectrometric analysis to be a compound expressed, denoting a methyl, ethyl and vinyl groups with Me, Et and Vi, respectively, by the structural formula

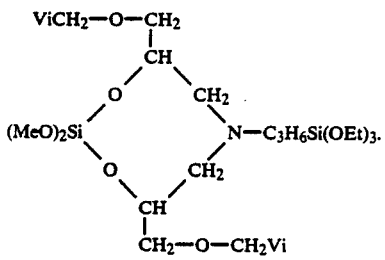

The above mentioned yield of this product was 38 % of the theoretical value. The Product II was stable in storage showing no changes after 1 month at 25° C.

PREPARATION 4

Into the same flask as used in Preparation 1 were introduced 259.9 g (1.1 moles) of 3-glycidyloxypropyl trimethoxysilane, 110.7 g (0.5 mole) of 3-aminopropyl triethoxysilane and 304.4 g (2.0 moles) of tetramethoxysilane and the mixture was heated at 100° to 110° C. under agitation for 4 hours. Stripping of the unreacted tetramethoxysilane by distillation of the reaction mixture at 110° to 120° C. under a reduced pressure of 5 mmHg gave 471.5 g of a product, which is referred to as the Product III hereinbelow, having a viscosity of 37.5 centistokes and a refractive index of 1.4409. The above mentioned yield was 90% of the theoretical value.

Comparative Preparation

Into the same flask as used in Preparation 1 were introduced 259.9 g (1.1 moles) of 3-glycidyloxypropyl trimethoxysilane and 110.7 g (0.5 mole) of 3-aminopropyl triethoxysilane and the mixture was heated at 100° to 110° C. under agitation for 3 hours. The reaction product, referred to as the Product IV hereinbelow, had a viscosity of 23.8 centistokes and a refractive index of 1.4534 and was unstable in storage to be gelled after 1 month at 25° C.

EXAMPLE 1

The Products I, II and III prepared in the above described Preparations were each dissolved in toluene to give a solution of 10% by weight concentration. These solutions are referred to as the Primers I, II and III, respectively, hereinbelow. Each of the Primers I, II and III was applied to the surface of a glass plate and an aluminum plate and each of the thus primer-treated test plates was coated with a polyurethane-based sealant (Takenate L-1025, a product by Takeda Yakuhin Kogyo Co.) followed by standing in atmospheric air at room temperature for 7 days to effect curing of the sealant. These test plates each with a cured sealant layer on the surface were subjected to the test of the adhesive bonding strength according to the procedure specified in JIS A 5754 either as cured, after subsequent dipping in water for 96 hours at 25° C. or after subsequent heating for 96 hours at 70° C. to give the results shown in Table 1 below together with the results obtained without using any primer.

EXAMPLE 2

The Primers I, II and III prepared and used in Example 1 were each applied to the surface of test plates of glass, aluminum, nickel, mild steel and iron and the thus primer-treated test plates were coated with a silicone-based sealant (KE 42, a product by Shin-Etsu Chemical Co.). After curing of the silicone sealant, the test of the shearing adhesive strength between the cured sealant layer and the test plate was undertaken to find that cohesive failure took place in each case within the layer of the cured sealant without peeling of the silicone layer.

EXAMPLE 3

A liquid silicone rubber composition was prepared by uniformly blending 100 parts by weight of a dimethylpolysiloxane having a viscosity of 5000 centistokes and terminated at both molecular chain ends each with a silanolic hydroxy group, 2.5 parts by weight of an organopolysiloxane resin composed of monofunctional trimethylsiloxy units $(CH_3)_3SiO_{0.5}$ and tetrafunctional $SiO_2$ units, 10 parts by weight of a quartz powder having an average particle diameter of 4 $\mu$m, 38 parts by weight of calcium carbonate filler having an average particle diameter of 0.1 $\mu$m and 1 part by weight of ethyl polysilicate.

TABLE 1

| Test plate | Primer No. | Adhesive bonding strength, kg/cm² | | |
|---|---|---|---|---|
| | | As cured | After dipping in water | After heating at 70° C. |
| Glass | None | 4.2 | 2.6 | 8.5 |
| | I | 6.5 | 6.6 | 13.5 |
| | II | 5.7 | 6.0 | 12.1 |
| | III | 5.8 | 6.4 | 12.4 |
| Aluminum | None | 2.6 | 2.3 | 5.7 |
| | I | 6.0 | 6.0 | 11.0 |
| | II | 6.6 | 8.6 | 11.2 |
| | III | 6.4 | 7.3 | 10.7 |

The thus prepared liquid silicone rubber composition was admixed with 2% by weight of a 32:3 by weight mixture of the Product III obtained in the Preparation 4 and dibutyltin dilaurate to give a curable liquid silicone rubber composition which was applied to the surfaces of test plates of aluminum, glass, polyester resin, epoxy resin and acrylic resin and kept standing for 3 days at room temperature to effect curing. The examination of the adhesion between the thus cured silicone rubber layer and the test plates indicated that the adhesion was complete in each of the test plates excepting the plate of the acrylic resin.

What is claimed is:

1. An adhesion promotor for a rubbery sealant composition which is a reaction product of a reaction mixture comprising:

(a) 1 mole of an organic amine compound having at least one active hydrogen atom in a molecule or an aminoalkyl alkoxysilane compound;

(b) from 0.5 to 4 moles of an organic compound having at least one epoxy group in a molecule or an epoxyalkyl alkoxysilane compound; and (c) from 0.5 to 12 moles of an alkoxysilane represented by the general formula $R^1_a Si(OR^2)_{4-a}$, in which $R^1$ is a hydrogen atom or a monovalent hydrocarbon group having 1 to 4 carbon atoms, $R^2$ is a monovalent hydrocarbon group having 1 to 4 carbon atoms or an alkoxy-substituted alkyl group and a is a number of zero, 1, 2 or 3, or a partial hydrolysis product thereof, at least one of the components (a) and (b) being an aminoalkyl alkoxysilane or an epoxyalkyl alkoxysilane, respectively.

* * * * *